United States Patent [19]

Roane

[11] Patent Number: 4,990,090
[45] Date of Patent: Feb. 5, 1991

[54] ENDODONTIC POST CONSTRUCTION

[76] Inventor: James B. Roane, 707 Southwest 24th St., Ste. 201, Norman, Okla. 73069

[21] Appl. No.: 562,416

[22] Filed: Jul. 30, 1990

Related U.S. Application Data

[63] Continuation of Ser. No. 274,305, Nov. 18, 1988, abandoned.

[51] Int. Cl.$^5$ .............................................. A61C 5/08
[52] U.S. Cl. ....................................... 433/220; 433/221
[58] Field of Search ................. 433/173, 220, 221, 225

[56] References Cited

U.S. PATENT DOCUMENTS

| D. 273,984 | 5/1984 | Vlock | 433/225 |
|---|---|---|---|
| 347,975 | 8/1886 | Starr | 433/220 |
| 371,053 | 10/1887 | Gates | 433/221 |
| 430,522 | 6/1890 | Genese | 433/221 |
| 636,568 | 11/1899 | Seeley | 433/221 |
| 644,803 | 3/1900 | Justi | 433/220 |
| 732,922 | 7/1903 | Clark | 433/221 |
| 758,750 | 5/1904 | Haldeman | 433/221 |
| 1,119,407 | 12/1914 | Davis | 433/225 |
| 1,218,289 | 3/1917 | Maker | 433/220 |
| 3,386,169 | 6/1968 | Scialom | 433/173 |
| 3,590,486 | 7/1971 | Brenner et al. | 433/225 |
| 3,675,328 | 7/1972 | Weissman | 433/225 |
| 3,675,329 | 7/1972 | Weissman | 433/225 |
| 3,728,794 | 4/1973 | Edelman | 433/225 |
| 3,740,851 | 6/1973 | Weissman | 433/225 |
| 3,790,507 | 2/1974 | Hodosh | 433/173 |
| 3,861,043 | 1/1975 | Lieb et al. | 433/225 |
| 3,874,081 | 4/1975 | Franklin et al. | 433/225 |
| 4,060,896 | 12/1977 | Wahnish | 433/174 |
| 4,229,169 | 10/1980 | Smith et al. | 433/174 |
| 4,234,309 | 11/1980 | Sellers | 433/225 |
| 4,259,076 | 3/1981 | Yanney | 433/225 |
| 4,268,253 | 5/1981 | Gross et al. | 433/221 |
| 4,276,027 | 6/1981 | Lustig | 433/225 |
| 4,290,756 | 9/1981 | Sellers | 433/225 |
| 4,349,335 | 9/1982 | Weissman | 433/225 |
| 4,365,958 | 12/1982 | Vlock | 433/225 |
| 4,397,634 | 8/1983 | Biggs | 433/225 |
| 4,431,416 | 2/1984 | Niznick | 433/174 |
| 4,468,200 | 8/1984 | Munch | 433/174 |
| 4,479,783 | 10/1984 | Weissman | 433/221 |
| 4,490,116 | 12/1984 | Deutsch et al. | 433/215 |
| 4,500,296 | 2/1985 | Friedman | 433/225 |
| 4,579,532 | 4/1986 | Lustig | 433/225 |
| 4,600,392 | 7/1986 | Weissman | 433/225 |
| 4,655,711 | 4/1987 | Weissman | 433/225 |
| 4,708,655 | 11/1987 | Weissman | 433/225 |
| 4,713,004 | 12/1987 | Linkow et al. | 433/174 |
| 4,713,006 | 12/1987 | Hakamatsuka et al. | 433/201.1 |
| 4,729,736 | 3/1988 | Weissman | 433/221 |
| 4,758,160 | 7/1988 | Ismail | 433/173 |
| 4,767,332 | 8/1988 | Weissman | 433/225 |

FOREIGN PATENT DOCUMENTS

| 0700397 | 2/1931 | France | 433/220 |
|---|---|---|---|
| 0063613 | 9/1955 | France | 433/174 |
| 1113114 | 9/1984 | U.S.S.R. | 433/220 |

OTHER PUBLICATIONS

"Preparing Severely Damaged Teeth", Mar., 1983, CDA Journal, pp. 85–91 by Shillingburg, Jr. et al.

Primary Examiner—Robert P. Swiatek
Assistant Examiner—Adriene B. Lepiane
Attorney, Agent, or Firm—Laney, Dougherty, Hessin & Beavers

[57] ABSTRACT

An endodontic post construction is provided for anchoring a tooth restoration to a portion of a human tooth. At least first and second endodontic posts having first and second complementary surfaces are fitted together so that the posts together provide a generally non-circular cross-sectional shape which is resistive to rotation within a root canal of the tooth.

32 Claims, 3 Drawing Sheets

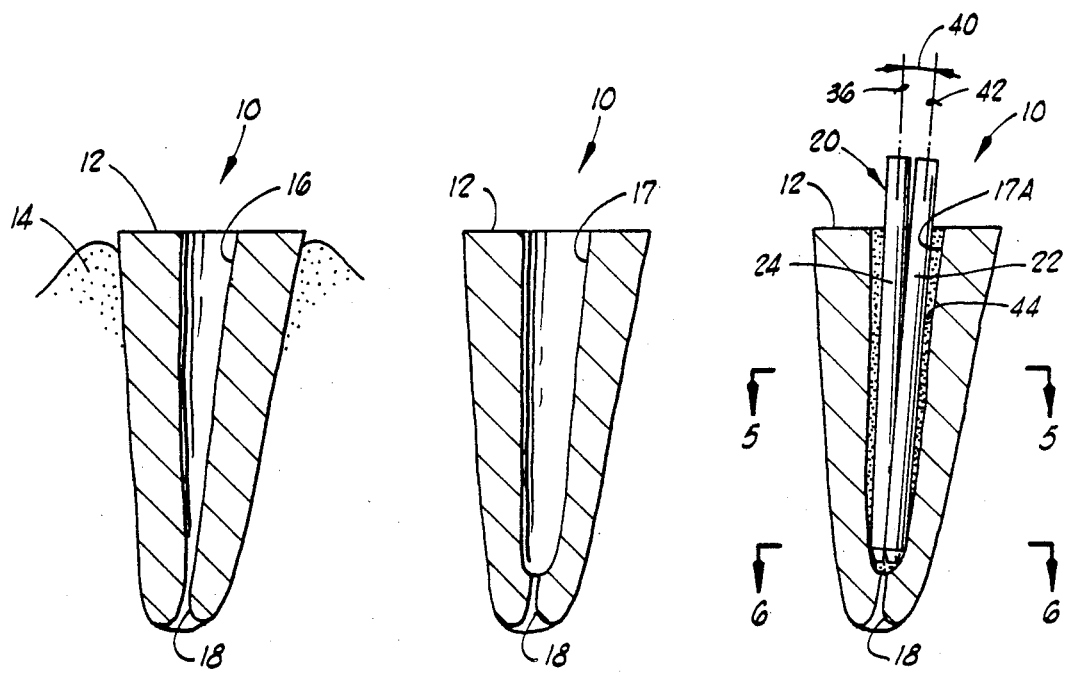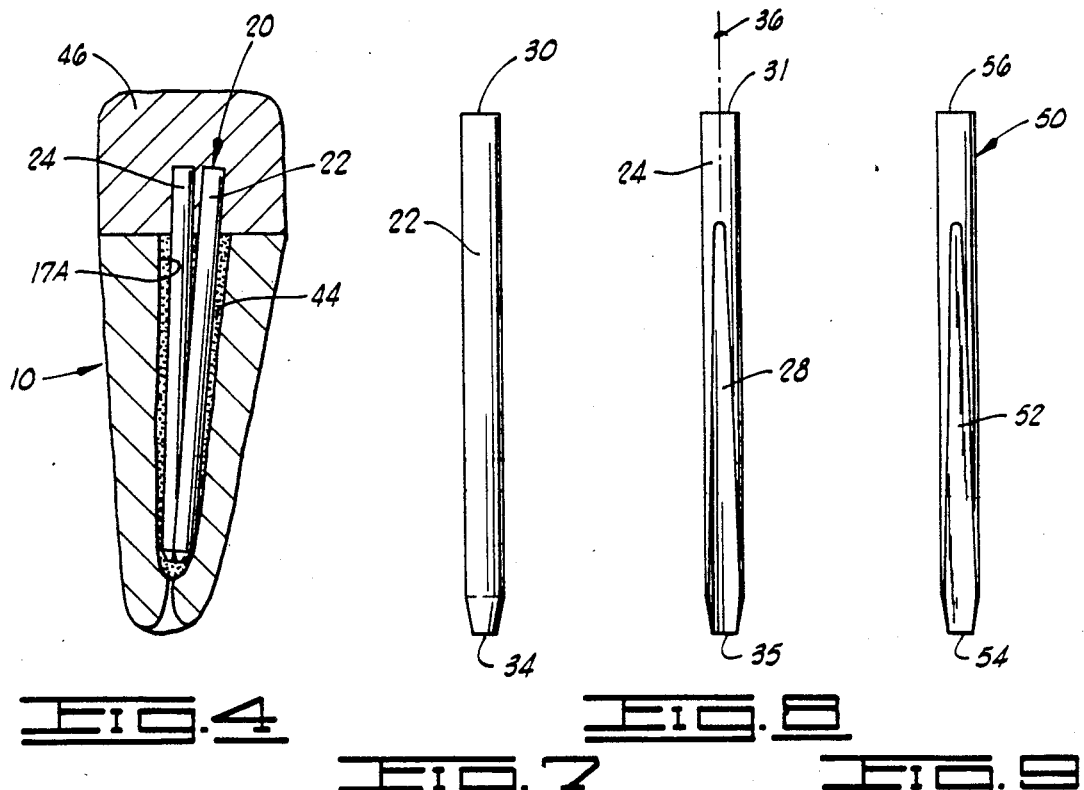

ENDODONTIC POST CONSTRUCTION

This is a continuation of copending application Ser. No. 07,274,305 filed on Nov. 18, 1988 and abandoned on July 30, 1990.

BACKGROUND OF THE INVENTION

1. Field Of The Invention

This invention relates to a dental post construction for use in anchoring a tooth restoration to a portion of an injured tooth.

2. Description Of The Prior Art

When repairing severely damaged teeth, a dental post is often utilized to help anchor a tooth restoration such as an artificial crown to a remaining root portion of a tooth. For example, the crown may be broken from a tooth by a traumatic injury or may have substantial portions thereof removed due to removal of decayed areas, thus leaving the root or roots of the tooth along with a relatively short stub of the original crown extending above the patient's gum area.

When the damage to the tooth is such that it is necessary to remove the pulp material from the root canals, it is common to use an endodontic post to help anchor the artificial crown to the remaining original tooth structure. An endodontic post is a cylindrical pin which is cemented into the endodontically prepared root canal and extends above the surface of the remaining natural tooth to serve as an anchor for the artificial crown restoration which is attached to the remaining natural tooth.

In multi-canaled teeth such as molars, there will typically be two such posts, one placed in each of two separate canals. In single-canaled teeth, typically a single cylindrical post will be placed in the canal.

A general description of these prior art procedures utilizing endodontic posts, both in multi-canaled and single-canaled teeth is provided in "Preparing Severely Damaged Teeth", March, 1983, *CDA Journal*, pages 85–91 by Shillingburg, Jr., et al.

The posts utilized for such tooth restorations are typically cylindrical, often having grooves, threads or flutes formed in the post for aid in cementing the post in place and/or venting cement from the root canal as the post is placed in the canal.

Typical prior art posts are disclosed in the Shillingburg, Jr., et al. article, and also in U.S. Pat. No. 4,479,783 to Weissman.

The difficulty with these prior art post constructions arises primarily in teeth having a single-canaled root. There, the use of a single cylindrical post cemented in place in the canal is sometimes unsuccessful, because the substantial forces applied to the artificial crown during biting and chewing may apply rotational forces to the crown about the longitudinal axis of the post, often causing rotation of the post within the canal and resulting in the artificial crown breaking away from the natural portion of the tooth.

One prior art multi-post construction is shown in U.S. Pat. No. 758,750 to Haldeman. The Haldeman structure, however, utilizes two semi-cylindrical posts which when fitted together result in a post construction having a circular cross section which still is susceptible to rotation within the root canal.

The prior art also includes irregularly shaped single-piece dental posts which are contoured to fill an oval-shaped upper portion of a root canal. For example, in U.S. Pat No. 4,600,392 to Weissman, a dental post is provided having projecting ribs on either side. A special jig must be utilized to drill the tooth canal to an appropriate shape to receive the contoured dental post.

Another dental post construction similar to that of the Weissman '392 patent is shown in U.S. Pat. No. 4,708,655 also to Weissman.

SUMMARY OF THE INVENTION

The present invention provides an improved and very effective endodontic post construction for anchoring a tooth restoration. This construction is particularly useful in teeth having a single-canaled root where a single cylindrical endodontic post as generally used is sometimes ineffective due to its inefficient resistance to rotation of the tooth restoration about the axis of the post. Also when the canal is oval shaped, the single cylindrical post does not effectively fill the prepared canal.

The endodontic post construction of the present invention provides at least first and second endodontic posts having first and second complementary surfaces, respectively, fitted together so that the posts together provide a generally non-circular cross-sectional shape which is resistive to rotation.

The endodontic posts each individually are generally cylindrical in shape. In the preferred embodiment, the second post has an outer surface interrupted by a concave generally longitudinal groove which has a crescent-shaped cross section in which a cylindrical outer surface of the first post is closely received. An acute angle is formed between a central axis of the first post and a central axis of the second post so that the cross-sectional shape of the combined first and second posts is generally longitudinally inwardly tapered. This provides an endodontic post construction which is easily adaptable by the dental practitioner to efficiently fill various irregular cross-sectional shapes of tooth canals.

No special drilling jigs or the like are required for the preparation of the root canal. No complex irregularly contoured posts are required.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 is an elevation cross section view of a tooth having a single-canaled root. The upper portion of the tooth has been broken off or removed.

FIG. 2 is a view of the tooth of FIG. 1, after the root canal has been endodontically prepared to form an endodontic post space for receiving a post construction.

FIG. 3 illustrates one embodiment of the post construction of the present invention cemented in place within the post space of FIG. 2.

FIG. 4 illustrates the post construction of FIG. 3 after a tooth restoration has been mounted on the tooth and anchored by the endodontic post construction.

FIG. 5A illustrates the embodiment seen in FIG. 3. FIGS. 5B and 5C illustrate two embodiments using three posts. FIG. 5D illustrates an embodiment utilizing two posts of an alternative design, and is representative of the view taken along line 5D—5D of FIG. 10.

FIG. 6A illustrates the embodiment seen in FIG. 3. FIGS. 6B and 6C illustrate two embodiments using three posts. FIG. 6D illustrates the embodiment utilizing two posts of an alternative design, and is representative of the view taken along line 6D—6D of FIG. 10.

FIG. 7 is an elevation view of an individual cylindrical endodontic post which does not contain a longitudinal groove.

FIG. 8 is an elevation view of an individual generally cylindrical endodontic post having a crescent-shaped longitudinal groove defined therein.

FIG. 9 is an elevation view of a generally cylindrical endodontic post having a flat longitudinal surface defined thereon. The post of FIG. 9 is utilized with the construction shown in FIG. 10 and in FIGS. 5D and 6D.

DETAILED DESCRIPTION OF THE PREFERRED EMBODIMENTS

Figure 5A:
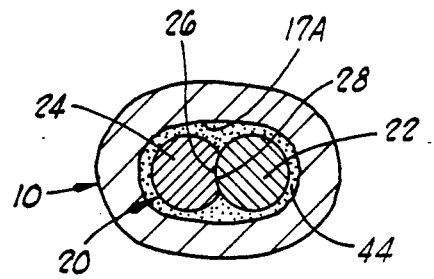
FIGS. 5A–5D are cross-sectional views as would be taken along a line 5—5 of FIG. 3, illustrating four different embodiments of the post construction.

FIG. 1 shows an elevation sectioned view of the remaining inward root and stub of a human tooth 10 having a single-canaled root. The tooth 10 has been broken off or modified such that it has an unfinished upper surface 12 extending somewhat above the patient's gum tissue 14.

The particular tooth illustrated has a single root canal 16 extending downward to an apical opening or apical foramen 18.

Prior to the placement of an endodontic post in the root canal 16, the canal 16 will be endodontically prepared in a manner well known to those skilled in the art through the use of endodontic files to enlarge the root canal 16 removing the pulp material therefrom and providing an enlarged prepared root canal also referred to as an endodontic post space 17 as seen in FIG. 2. This preparation of the root canal is done for the purpose of removing the pulp material, and also in the present instance to provide a more suitable receptacle for the endodontic post which will be placed in the prepared post space 17 to help anchor a tooth restoration. The root canal beyond the endodontic post space 17 is suitably sealed before placing the endodontic post.

In FIGS. 5A-5D variations of the prepared post space 17 are designated as 17A-17D, respectively.

As can be seen for example in FIG. 5A, which is a plan section view taken along line 5—5 of FIG. 3, the upper portions of the prepared post space 17A will typically be somewhat oval in shape. Lower portions of the post space as seen in FIG. 6A will typically be somewhat more circular in shape.

Figure 6A:
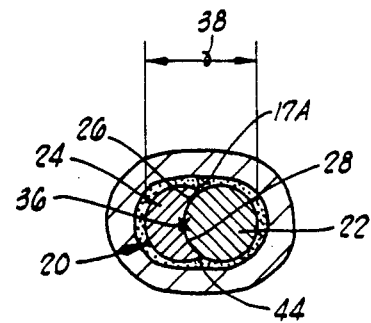
FIGS. 6A—6D are cross-sectional views as would be taken along a line 6—6 of FIG. 3, illustrating the four different embodiments of the post construction.

As seen in FIGS. 3, 5A and 6A, an endodontic post construction 20 includes a first endodontic post 22 and a second endodontic post 24 having first and second complementary surfaces 26 and 28, respectively, fitted together so that the posts 22 and 24 together provide a generally non-circular cross-sectional shape which is resistive to rotation in the post space 17A.

The cross-sectional shape of the post construction 20 of FIGS. 5A and 6A can generally be described as that of two overlapping, non-concentric, equal diameter circles.

The posts 22 and 24 are individually shown in FIGS. 7 and 8, respectively. Each of the posts is generally cylindrical in shape. First post 22 has longitudinally inner and outer ends 34 and 30. Second post 24 has longitudinally inner and outer ends 35 and 31.

The post 22 of FIG. 7 is shown as a smooth cylindrical post with no external interruptions, but that is merely for ease of illustration. The post 22 can in fact be any commonly available, generally cylindrical prior art dental post which typically will have flutes, threads, vent grooves or the like placed in its outer, generally cylindrical surface for aid in cementing the post 22 in place. For example, any of the posts illustrated in FIGS. 1-3 of U.S. Pat. No. 4,479,783 to Weissman could be utilized as the post 22.

The post 24 of FIG. 8 is similar to the post 22 of FIG. 7 except that it has been modified by addition of a concave generally longitudinal groove 28 which interrupts its generally cylindrical outer surface. The groove 28 is the previously mentioned second complementary surface.

As best seen in FIG. 6A, the concave groove 28 is generally crescent-shaped in cross section having a radius of curvature equal to a radius of the posts 22 and 24 so that a portion 26 of the generally cylindrical outer surface of the first post 22 is closely received within the groove 28.

Adjacent the longitudinally inner end 35 of the second post 24, the concave groove 28 extends laterally into the second post 24 to approximately a central axis 36 of second post 24. Thus, adjacent the lower ends 34 and 35 of posts 22 and 24, the post construction 20 has a maximum cross-sectional dimension 38 of approximately 1½ diameters of the posts 22 and 24.

The concave groove 28 becomes shallower as it approaches the longitudinally outer end 31 of second post 24. The groove 28 terminates short of the longitudinally outer end 31.

When the first and second posts 22 and 24 are fitted together as seen in FIG. 3, an acute angle 40 is formed between a central axis 42 of the first post 22 and the central axis 36 of second post 24 so that the cross-sectional shape of the combined first and second posts 22 and 24 is generally longitudinally inwardly tapered as is apparent in FIG. 3.

When the first and second posts 22 and 24 are fitted together, the groove 28 of second post 24 extends in a generally straight direction, generally parallel to the central axis 42 of the first post 22.

The acute angle 40 is preferably in a range of from about 7° to about 11°.

The central axis 42 of first post 22 can also be described as a longitudinal axis 42 of the crescent-shaped longitudinal groove 28 of second post 24 when the first and second posts 22 and 24 are fitted together. Thus, the angle 40 can also be defined as the angle between a central axis of second post 24 and a longitudinal axis of the groove 28.

A preferred manner of using the post construction 20 is as follows. After preparation of the post space 17 as shown in FIG. 2, the post space is filled with cement 44 as shown in FIG. 3 for post space 17A. Then, the first post 22 is inserted into the post space 17A and typically will be lodged adjacent one end of the oval-shaped post space 17A as best seen in FIG. 5A. Then, the second post 24 having the groove 28 defined therein is inserted into the post space 17A with the groove 28 fitted up against the cylindrical outer surface of first post 22. The second post 24 will be inserted into the post space 17A as shown in FIGS. 3 and 4.

The first and second posts 22 and 24 when fitted together provide a generally non-circular cross-sectional shape as seen in FIGS. 5A and 6A which is generally resistive to rotation within the prepared post space 17A.

Then, a tooth restoration 46 can be mounted upon the posts 22 and 24 as somewhat schematically illustrated in FIG. 4. It will be understood that the tooth restoration 46 may be of many different constructions which are well known to those skilled in the art.

ALTERNATIVE EMBODIMENT OF FIGS. 5B AND 6B

Figure 5B:
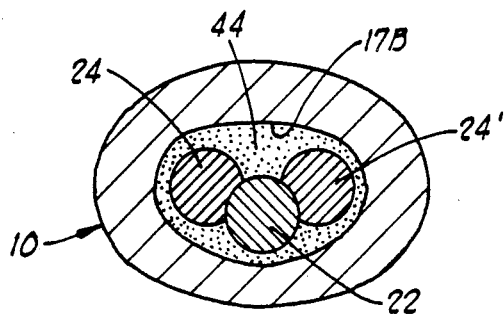

In some instances, the post space 17 of tooth 10 may have a somewhat triangular cross section 17B after the canal has been prepared, as is illustrated in FIG. 5B. In such an application, it may be desirable to utilize a third endodontic post 24' which is identical to the second post 24.

Figure 6B:
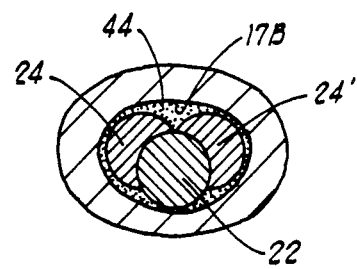

The second and third posts 24 and 24' will generally be arranged to circumferentially abut at their longitudinally inward ends as generally illustrated in FIG. 6B so as to provide a somewhat triangular overall cross section to generally fill the triangular cross section post space 17B.

ALTERNATIVE EMBODIMENT OF FIGS. 5C AND 6C

Figure 5C:
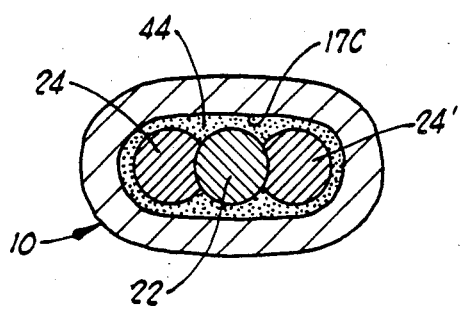

Yet another situation which is sometimes encountered is a very elongated, generally oval cross section 17C of the post space as illustrated in FIG. 5C.

Figure 6C:
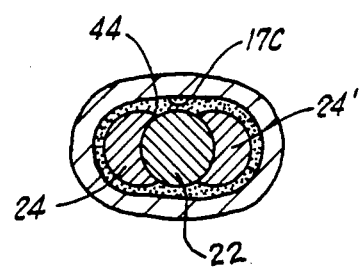

This situation also can be treated by the addition of a third endodontic post 24'. In this situation, the first and third posts 24 and 24' are located on diametrically opposite sides of the first post 22 as seen in FIGS. 5C and 6C. An acute angle will be formed between the central axes of the second and third posts 24 and 24' which is approximately twice the angle 40 previously described with reference to FIG. 3.

ALTERNATIVE EMBODIMENT OF FIGS. 5D, 6D, 9 AND 10

Figure 10:
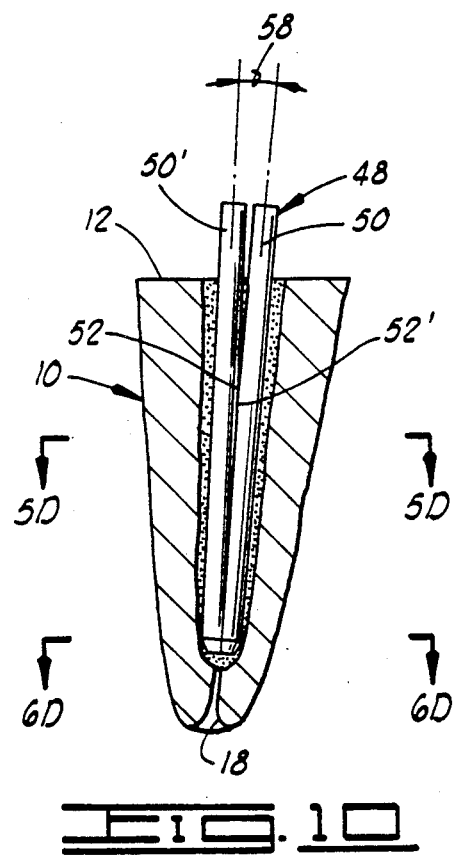
FIG. 10 is an elevation view similar to FIG. 3 of one of the alternative embodiments of the present invention utilizing two posts like the post of FIG. 9. The cross-sectional details of the embodiment of FIG. 10 are seen in FIGS. 5D-6D.

In FIG. 10, an alternative endodontic post construction 48 is shown utilizing first and second endodontic posts 50 and 50' which are generally identical in shape, and which have essentially identical flat first and second complementary surfaces 52 and 52' defined thereon.

Figure 5D:
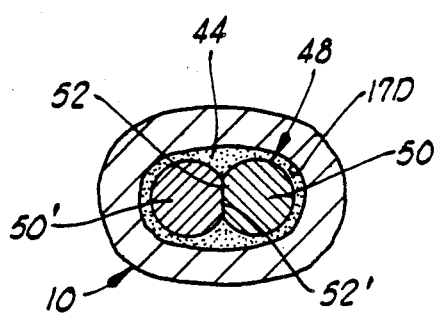
Figure 6D:
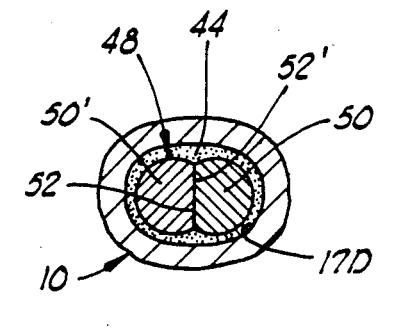

As seen in FIGS. 5D and 6D, the particular alternative post construction 48 is shown in a generally oval cross section prepared post space 17D which is essentially identical to the oval cross-section post space 17A of FIGS. 5A and 6A.

The post 50 is best shown in FIG. 9. The post 50 has a longitudinally inward end 54 and a longitudinally outward end 56. The flat surface 52 extends generally from the longitudinally inward end 54 and terminates short of the longitudinally outward end 56 in a manner similar to that previously described for the orientation of the groove 28 of post 24 shown in FIG. 8.

The flat surface 52 of the post 50 is non-parallel to a central axis of the post 50 so that when the two posts 50 and 50' are fitted together as shown in FIG. 10, an acute angle 58 is defined between the longitudinal axes thereof. The angle 58 is analogous to the angle 40 previously described with regard to FIG. 3, and preferably is within the same general range of values.

The first embodiment illustrated in FIG. 3 is generally preferred since the use of the groove 28 which receives the outer surface of the first post 22 tends to somewhat lock the first and second posts 22 and 24 together. Although it is not a positive interlock, it will generally serve to hold the two posts 22 and 24 together since the posts are generally wedged together in the lower portion of the prepared root canal 17A. Also, it aids in preventing slippage of the post construction when rotational forces are applied to the tooth restoration 46.

The alternative embodiment of FIG. 10, however, can also be utilized although more care may be required to properly fit the posts 50 and 50' together since the flat complementary surfaces 52 and 52' may slide laterally relative to each other.

The post 50, however, may be more easily manufactured than the post 24, and thus for that reason may in some instances be preferred.

Thus, it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. An endodontic post construction for anchoring a tooth restoration, comprising:
    at least first and second generally cylindrical endodontic posts of substantially equal diameters having first and second complementary surfaces, respectively, fitted together to form a generally longitudinal contact surface so that said posts together provide a generally non-circular cross-sectional shape which is resistive to rotation.
2. The post construction of claim 1, wherein:
    said second post has an outer surface interrupted by a generally longitudinal concave groove in which a portion of an outer surface of said first post is received, said portion of said outer surface of said first post and said groove being said first and second complementary surfaces, respectively.
3. The post construction of claim 2, wherein:
    said concave groove extends laterally into said second post to approximately a central axis of said second post at a longitudinally inner end of said second post.
4. The post construction of claim 3, wherein:
    an acute angle is formed between a central axis of said first post and said central axis of said second post so that said cross-sectional shape of said combined first and second posts is generally longitudinally inwardly tapered.
5. The post construction of claim 4, wherein:
    said groove extends in a generally straight direction generally parallel to said central axis of said first post such that said groove becomes shallower as it approaches a longitudinally outer end of said second post and such that said groove terminates short of said longitudinally outer end of said second post.
6. The post construction of claim 4, wherein:

said acute angle is in a range of from about 7° to about 11°.

7. The post construction of claim 2, wherein:
said groove of said second post becomes shallower as it approaches a longitudinally outer end of said second post.

8. The post construction of claim 7, wherein:
said groove terminates short of said longitudinally outer end of said second post.

9. The post construction of claim 7, wherein:
said concave groove is generally crescent shaped in cross section.

10. The post construction of claim 2, wherein:
said concave groove is generally crescent shaped in cross section so as to closely receive said portion of said cylindrical outer surface of said first post.

11. THe post construction of claim 1, wherein:
said first and second complementary surfaces are flat.

12. The post construction of claim 11, wherein:
said first and second posts are generally identical in shape.

13. The post construction of claim 11, wherein:
said flat first and second complementary surfaces are non-parallel to central axes of said first and second posts, respectively.

14. The post construction of claim 1, further comprising:
a third endodontic post having a third surface defined thereon complementary to a fourth surface defined on said first post, said third and fourth surfaces being fitted together so that said three posts together provide said rotationally resistive, generally non-circular cross-sectional shape.

15. The post construction of claim 14, wherein:
said third post is located on an opposite side of said first post from said second post; and
an acute angle is formed between a central axis of said second post and a central axis of said third post so that said cross-sectional shape of said combined first, second and third posts is generally longitudinally inwardly tapered.

16. The post construction of claim 1, wherein:
said first and second complementary surfaces are so arranged and constructed that when said two posts are fitted together said cross-sectional shape is longitudinally inwardly tapered.

17. An endodontic post, comprising:
a generally cylindrical outer surface interrupted by an arcuate cross section concave generally longitudinal linear groove having a radius of curvature substantially equal to a radius of said cylindrical outer surface.

18. The post of claim 17, wherein:
said concave groove extends laterally into said post to approximately a central axis of said post at a longitudinally inner end of said post.

19. The post of claim 17, wherein:
an acute angle is formed between a central axis of said post and a longitudinal axis of said groove.

20. The post of claim 19, wherein:
said acute angle is in a range of from about 7° to about 11°.

21. The post of claim 19, wherein:
said groove becomes shallower as it approaches a longitudinally outer end of said post and terminates short of said longitudinally outer end of said post.

22. The post of claim 21, wherein:
said concave groove extends laterally into said post to approximately a central axis of said post at a longitudinally inner end of said post.

23. The post of claim 19, wherein:
said groove become shallower as it approaches a longitudinally outer end of said post and terminates short of said longitudinally outer end of said post.

24. The post of claim 23, wherein:
said concave groove extends laterally into said post to approximately a central axis of said post at a longitudinally inner end of said post.

25. A method of anchoring a tooth restoration, said method comprising the steps of:
(a) providing at least first and second generally cylindrical endodontic posts of substantially equal diameters having first and second complementary surfaces, respectively;
(b) fitting said first and second complementary surfaces of said at least first and second posts together to provide a generally non-circular cross-sectional shape;
(c) cementing said at least first and second posts into a prepared root canal of a tooth, said non-circular cross-sectional shape being resistive to rotation within said prepared root canal; and
(d) mounting said tooth restoration on said at least first and second posts.

26. The method of claim 25, wherein:
step (b) includes a step of forming an acute angle between a central axis of said first post and a central axis of said second post so that said cross-sectional shape is longitudinally inwardly tapered.

27. The method of claim 25, wherein:
step (a) is further characterized in that said second post has a generally cylindrical outer surface interrupted by a generally concave longitudinal groove in which a portion of an outer surface of said first post is received, said portion of said outer surface of said first post and said groove being said first and second complementary surfaces, respectively.

28. The method of claim 27, wherein:
step (a) is further characterized in that said groove is generally crescent shaped in cross section so as to closely receive said portion of said cylindrical outer surface of said first post.

29. The method of claim 25, wherein:
steps (b) and (c) are further characterized in that said first post is inserted into said prepared root canal and then said second post is inserted into said prepared root canal and said first and second complementary surfaces are fitted together within said prepared root canal.

30. The method of claim 29, wherein:
step (c) is further characterized in that said prepared root canal is filled with cement prior to inserting said first and second posts into said prepared root canal.

31. The method of claim 25, wherein:
step (c) is further characterized in that said prepared root canal is a root canal of a single-canaled root of said tooth.

32. An endodontic post construction for anchoring a tooth restoration, comprising:
first and second endodontic posts having first and second complementary surfaces, respectively, fitted together so that said posts together provide a generally non-circular, cross-sectional shape which is resistive to rotation;

a third endodontic post having a third surface defined thereon complementary to a fourth surface defined on said first post, said third and fourth surfaces being fitted together so that said three posts together provide said rotationally resistive, generally non-circular, cross-sectional shape;

wherein said first post has a generally cylindrical outer surface, diametrically opposed portions of which define said first and fourth surfaces;

wherein said second post has a partially cylindrical outer surface interrupted by a generally longitudinal concave groove in which said first surface of said first post is received; and wherein said third post has a partially cylindrical outer surface interrupted by a generally longitudinally concave groove in which said fourth surface of said first post is received, said first and third posts being located on diametrically opposite sides of said first post.

* * * * *

UNITED STATES PATENT AND TRADEMARK OFFICE
CERTIFICATE OF CORRECTION

PATENT NO. : 4,990,090
DATED : February 5, 1991
INVENTOR(S) : James B. Roane

It is certified that error appears in the above-identified patent and that said Letters Patent is hereby corrected as shown below:

Column 7, line 53;
    Claim 17, after "surface" and before the period, insert --whereby said groove can receive a second cylindrical post having an outer surface with a radius equal to that of the cylindrical outer surface of said endodontic post--.

Column 8;
    Claim 23, line 1, delete "19" and insert --17-- therefor.

Claim 32, third line from end, delete "first" and insert --second-- therefor.

Signed and Sealed this

Second Day of June, 1992

Attest:

DOUGLAS B. COMER

*Attesting Officer*    *Acting Commissioner of Patents and Trademarks*